United States Patent
Hagimoto et al.

(10) Patent No.: US 9,594,065 B2
(45) Date of Patent: Mar. 14, 2017

(54) APPARATUS FOR DETECTING DETERIORATION OF NOX SELECTIVE REDUCTION CATALYST

(75) Inventors: Taiga Hagimoto, Suntou-gun (JP); Daisuke Shibata, Numazu (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 14/110,636

(22) PCT Filed: Apr. 12, 2011

(86) PCT No.: PCT/JP2011/059092
§ 371 (c)(1),
(2), (4) Date: Oct. 8, 2013

(87) PCT Pub. No.: WO2012/140739
PCT Pub. Date: Oct. 18, 2012

(65) Prior Publication Data
US 2014/0050623 A1    Feb. 20, 2014

(51) Int. Cl.
*G01N 31/10* (2006.01)
*F01N 11/00* (2006.01)
*F01N 3/20* (2006.01)

(52) U.S. Cl.
CPC .............. *G01N 31/10* (2013.01); *F01N 3/206* (2013.01); *F01N 3/2066* (2013.01); *F01N 11/00* (2013.01);
(Continued)

(58) Field of Classification Search
CPC ..... Y02T 10/40; F01N 2610/02; F01N 3/208; F01N 2560/026; F01N 2560/021;
(Continued)

(56) References Cited

U.S. PATENT DOCUMENTS

2008/0306673 A1* 12/2008 Yasui et al. ................ 701/102
2010/0005873 A1*  1/2010 Katoh et al. ............. 73/114.75
(Continued)

FOREIGN PATENT DOCUMENTS

CN     101918686 A    12/2010
JP     2008-144711 A   6/2008
(Continued)

*Primary Examiner* — Dennis M White
*Assistant Examiner* — Bryan Kilpatrick
(74) *Attorney, Agent, or Firm* — Sughrue Mion, PLLC

(57) ABSTRACT

Apparatus for detecting deterioration of an NOx selective reduction catalyst in an exhaust passage of an internal combustion engine with improved accuracy, includes an NOx purification rate calculation unit for calculating the NOx purification rate in the NOx selective reduction catalyst based on the NOx concentration in the exhaust gas flowing into and out of the NOx selective reduction catalyst. A determination as to whether the NOx selective reduction catalyst is deteriorated is made based on the NOx purification rate at a time when the temperature of the NOx selective reduction catalyst is equal to or higher than a temperature (Tc0) at which the NOx purification rate will start to decrease with a rise in the temperature of the NOx selective reduction catalyst if the degree of deterioration of the NOx selective reduction catalyst is at the upper limit of an allowable range.

5 Claims, 6 Drawing Sheets

(52) U.S. Cl.
CPC ........ *F01N 11/002* (2013.01); *F01N 2550/02* (2013.01); *F01N 2560/021* (2013.01); *F01N 2560/026* (2013.01); *F01N 2560/06* (2013.01); *F01N 2560/14* (2013.01); *F01N 2610/02* (2013.01); *F01N 2900/1602* (2013.01); *F01N 2900/1621* (2013.01); *Y02T 10/24* (2013.01); *Y02T 10/47* (2013.01)

(58) Field of Classification Search
CPC .... F01N 11/00; F01N 2900/1622; F01N 9/00; F01N 2560/02; F01N 2560/00; F01N 2900/1806; F01N 2550/00; B01D 53/9418; B01D 53/9422; F02D 2041/1468; F02D 41/1463; F02D 41/1475; G01N 31/10; G01N 33/0054
USPC ............... 422/68.1, 82.12, 83, 111; 423/212; 73/114.71
See application file for complete search history.

(56) References Cited

U.S. PATENT DOCUMENTS

| | | | |
|---|---|---|---|
| 2010/0083637 A1* | 4/2010 | Sawada et al. | 60/277 |
| 2010/0101218 A1* | 4/2010 | Gabe et al. | 60/286 |
| 2012/0006002 A1 | 1/2012 | Hagimoto et al. | |

FOREIGN PATENT DOCUMENTS

| | | |
|---|---|---|
| JP | 2009-127496 A | 6/2009 |
| WO | WO 2008108499 A1 * | 9/2008 |

* cited by examiner

APPARATUS FOR DETECTING DETERIORATION OF NOX SELECTIVE REDUCTION CATALYST

CROSS REFERENCE TO RELATED APPLICATIONS

This application is a National Stage of International Application No. PCT/JP2011/059092 filed Apr. 12, 2011, the contents of all of which are incorporated herein by reference in their entirety.

TECHNICAL FIELD

The present invention relates to a deterioration detection apparatus for detecting deterioration of an NOx selective reduction catalyst provided in an exhaust passage of an internal combustion engine.

BACKGROUND ART

There has been a known technique of providing an NOx selective reduction catalyst (which will be sometimes referred to simply as an "NOx catalyst" hereinafter) as an exhaust purifying catalyst in an exhaust passage of an internal combustion engine. The NOx catalyst has the function of reducing NOx contained in the exhaust gas mainly using ammonia as a reducing agent. Various techniques for detecting deterioration of the NOx catalyst have been developed.

In the technique described in Patent Document 1, an abnormality of the NOx catalyst is determined based on the difference between the NOx purification rate at a time when the activity of the NOx catalyst is relatively low and the NOx purification rate at a time when the activity of the NOx catalyst is sufficiently high.

In the technique described in Patent Document 2, reducing agent is supplied to the NOx catalyst until ammonia leaks to the exhaust passage downstream of the NOx catalyst at a time when the temperature of the NOx catalyst is in a predetermined temperature range that is lower than the NOx removal temperature range and included in the ammonia absorption temperature range. A determination as to whether the NOx catalyst is deteriorated or not is made based on the total amount of reducing agent supplied to the NOx catalyst.

PRIOR ART DOCUMENT

Patent Document

Patent Document 1: Japanese Patent Application Laid-Open No. 2008-144711
Patent Document 2: Japanese Patent Application Laid-Open No. 2009-127496

DISCLOSURE OF THE INVENTION

Problem to be Solved by the Invention

An object of the present invention is to detect deterioration of an NOx selective reduction catalyst provided in an exhaust passage of an internal combustion engine with improved accuracy.

Means for Solving the Problem

In the first invention, a determination as to deterioration of an NOx catalyst is made based on the NOx purification rate in the NOx catalyst at a time when the temperature of the NOx catalyst is not lower than a temperature at which the NOx purification rate starts to decrease with a rise in the temperature of the NOx catalyst if the degree of deterioration of the NOx catalyst is at the upper limit of an allowable range.

More specifically, an apparatus for detecting deterioration of NOx selective reduction catalyst according to the present invention is an apparatus that detects deterioration of an NOx selective reduction catalyst provided in an exhaust passage of an internal combustion engine and comprises:

a temperature obtaining unit that obtains the temperature of the NOx selective reduction catalyst;

an NOx purification rate calculation unit that calculates the NOx purification rate in said NOx selective reduction catalyst based on the NOx concentration in the exhaust gas flowing into said NOx selective reduction catalyst and the NOx concentration in the exhaust gas flowing out of said NOx selective reduction catalyst; and a determination unit that determines whether or not said NOx selective reduction catalyst is deteriorated based on the NOx purification rate calculated by said NOx purification rate calculation unit at a time when the temperature of said NOx selective reduction catalyst is higher than a predetermined temperature, wherein said predetermined temperature is a temperature at which the NOx purification rate will start to decrease with a rise in the temperature of said NOx selective reduction catalyst if the degree of deterioration of said NOx selective reduction catalyst is at the upper limit of an allowable range.

The NOx purification rate mentioned here refers to the rate of the quantity of NOx reduced by the NOx catalyst to the quantity of NOx flowing into the NOx catalyst. The determination unit determines that the NOx catalyst is deteriorated if the degree of deterioration of the NOx catalyst is higher than the upper limit of an allowable range. The allowable range of the degree of deterioration of the NOx catalyst can be determined in advance based on, for example, an experiment.

The NOx catalyst has the function of reducing NOx using ammonia as a reducing agent and also has the function of oxidizing ammonia. The NOx reducing ability and the ammonia oxidizing ability of the NOx catalyst are both enhanced as the temperature of the NOx catalyst rises. When the temperature of the NOx catalyst is relatively low, the NOx reducing ability is higher than the ammonia oxidizing ability. When the temperature of the NOx catalyst is higher than a certain temperature, the ammonia oxidizing ability is higher than the NOx reducing ability. The oxidation of ammonia generates NOx. In consequence, when the ammonia oxidizing ability of the NOx catalyst becomes higher than the NOx reducing ability, the NOx purification rate in the NOx catalyst decreases. Therefore, when the temperature of the NOx catalyst reaches a certain temperature, the NOx purification rate starts to decrease with a rise in the temperature of the NOx catalyst.

The NOx reducing ability of the NOx catalyst is degraded as the deterioration of the NOx catalyst progresses. On the other hand, the ammonia oxidizing ability of the NOx catalyst is hard to be degraded even if the deterioration of the NOx catalyst progresses. Consequently, as the degree of deterioration of the NOx catalyst increases, the temperature of the NOx catalyst at which the ammonia oxidizing ability exceeds the NOx reducing ability becomes lower, namely the temperature (which will be herein after referred to as the NOx purification rate decrease temperature) at which the NOx purification rate starts to decrease with a rise in the temperature of the NOx catalyst becomes lower.

In view of the above, in the present invention, the determination unit determines whether the NOx catalyst is deteriorated or not based on the NOx purification rate at a time when the temperature of the NOx catalyst is higher than a predetermined temperature, which is the NOx purification rate decrease temperature with the NOx catalyst of which the decree of deterioration is at the upper limit of the allowable range (or the NOx purification rate decrease temperature that the NOx catalyst will have when the degree of deterioration thereof is at the upper limit of the allowable range).

In doing so, the determination unit may determine that the NOx catalyst is deteriorated if the NOx purification rate is lower than a predetermined threshold value. The predetermined threshold in this case may be the NOx purification rate in the NOx catalyst of which the degree of deterioration is at the upper limit of the allowable range.

When the temperature of the NOx catalyst is higher than the aforementioned predetermined temperature, the difference between the NOx purification rate in the NOx catalyst in a normal condition and the NOx purification rate in the NOx catalyst in a deteriorated condition becomes larger. Therefore, deterioration of the NOx catalyst can be detected with higher accuracy according to the present invention.

In the present invention, the determination unit may make a determination as to deterioration of the NOx catalyst at a time when the temperature of the NOx catalyst is equal to the NOx purification rate decrease temperature with the NOx catalyst in an initial condition. The initial condition mentioned here refers to a condition in which the degree of deterioration of the NOx catalyst is substantially equal to that at the time when the NOx catalyst is installed in the vehicle, namely a condition in which heat deterioration of the NOx catalyst has progressed little.

The NOx purification rate decrease temperature with the NOx catalyst in the initial condition is higher than the aforementioned predetermined temperature. When the temperature of the NOx catalyst is higher than the NOx purification rate decrease temperature with the NOx catalyst in the initial condition, the difference between the NOx purification rate in the NOx catalyst in a normal condition and the NOx purification rate in the NOx catalyst in a deteriorated condition gradually decreases as the temperature of the NOx catalyst rises. Therefore, if the determination as to deterioration of the NOx catalyst is performed at a time when the temperature of the NOx catalyst is equal to the NOx purification rate decrease temperature with the NOx catalyst that is in the initial condition (or the NOx purification rate decrease temperature that the NOx catalyst will have when it is in the initial condition), the determination as to deterioration of the NOx catalyst can be performed at the time when the difference between the NOx purification rate in the NOx catalyst in a normal condition and the NOx purification rate in the NOx catalyst in a deteriorated condition is as large as possible.

In the present invention, the determination unit may make a determination as to deterioration of the NOx catalyst at a time when the temperature of the NOx catalyst is higher than the aforementioned predetermined temperature and not higher than a temperature at which the NOx purification rate in the NOx catalyst will become zero if the degree of deterioration of the NOx catalyst is at the upper limit of the allowable range.

If the temperature of the NOx catalyst of which the degree of deterioration is at the upper limit of the allowable range rises beyond the predetermined temperature, the NOx purification rate decreases with the rise in the temperature. Eventually, the NOx purification rate becomes zero when the temperature of the NOx catalyst reaches a certain temperature. In the temperature range higher than the temperature at which the NOx purification rate in the NOx catalyst of which the degree of deterioration is at the upper limit of the allowable range will become zero, the NOx purification rate is zero if the NOx catalyst is deteriorated. On the other hand, even when the degree of deterioration of the NOx catalyst is lower than the upper limit of the allowable range, the NOx purification rate starts to decrease with a rise in the temperature of the NOx catalyst as the temperature of the NOx catalyst rises beyond the aforementioned predetermined temperature to reach the NOx purification rate decrease temperature corresponding to the degree of deterioration.

In the temperature range in which the NOx purification rate is zero when the degree of deterioration of the NOx catalyst is higher than the upper limit of the allowable range (namely, when the NOx catalyst is deteriorated), and the NOx purification rate decreases with a rise in the temperature of the NOx catalyst when the degree of deterioration of the NOx catalyst is lower than the upper limit of the allowable range (namely, when the NOx catalyst is in a normal condition), the difference between the NOx purification rate in the NOx catalyst in a normal condition and the NOx purification rate in the NOx catalyst in a deteriorated condition gradually decreases as the temperature of the NOx catalyst rises.

Therefore, if the determination as to deterioration of the NOx catalyst is performed at a time when the temperature of the NOx catalyst is higher than the aforementioned predetermined temperature and not higher than the temperature at which the NOx purification rate in the NOx catalyst of which the degree of deterioration is at the upper limit of the allowable range will become zero, the determination as to deterioration of the NOx catalyst can be performed at the time when the difference between the NOx purification rate in the NOx catalyst in a normal condition and the NOx purification rate in the NOx catalyst in a deteriorated condition is as large as possible.

According to a second invention, a determination as to deterioration of an NOx catalyst is performed based on the NOx purification rate decrease temperature.

More specifically, an apparatus for detecting deterioration of an NOx selective reduction catalyst according to the present invention comprises:

a temperature obtaining unit that obtains the temperature of the NOx selective reduction catalyst;

an NOx purification rate calculation unit that calculates the NOx purification rate in said NOx selective reduction catalyst based on the NOx concentration in the exhaust gas flowing into said NOx selective reduction catalyst and the NOx concentration in the exhaust gas flowing out of said NOx selective reduction catalyst; and a determination unit that determines that said NOx selective reduction catalyst is deteriorated if the temperature of said NOx selective reduction catalyst at which the NOx purification rate starts to decrease with a rise in the temperature of said NOx selective reduction catalyst is lower than a predetermined criterion temperature.

The predetermined temperature mentioned above may be the NOx purification rate decrease temperature with the NOx catalyst of which the degree of deterioration is at the upper limit of the allowable range.

As described above, the higher the degree of deterioration of the NOx catalyst is, the lower the temperature of the NOx catalyst at which the ammonia oxidizing ability becomes higher than the NOx reducing ability is, or the lower the NOx purification rate decrease temperature is. Therefore, if the NOx purification rate decrease temperature is lower than a predetermined criterion temperature, it may be determined that the NOx catalyst is deteriorated.

According to the present invention, deterioration of an NOx catalyst can be detected with improved accuracy.

Advantageous Effect of the Invention

According to the present invention, deterioration of an NOx selective reduction catalyst provided in an exhaust passage of an internal combustion engine can be detected with improved accuracy.

MODES FOR CARRYING OUT THE INVENTION

In the following, specific embodiments of the present invention will be described with reference to the drawings. The dimensions, materials, shapes and relative arrangements etc. of the component that will be described in connection with the embodiments are not intended to limit the technical scope of the present invention only to them, unless particularly stated.

<Embodiment 1>

[General Configuration of Exhaust System of Internal Combustion Engine]

Figure 1:
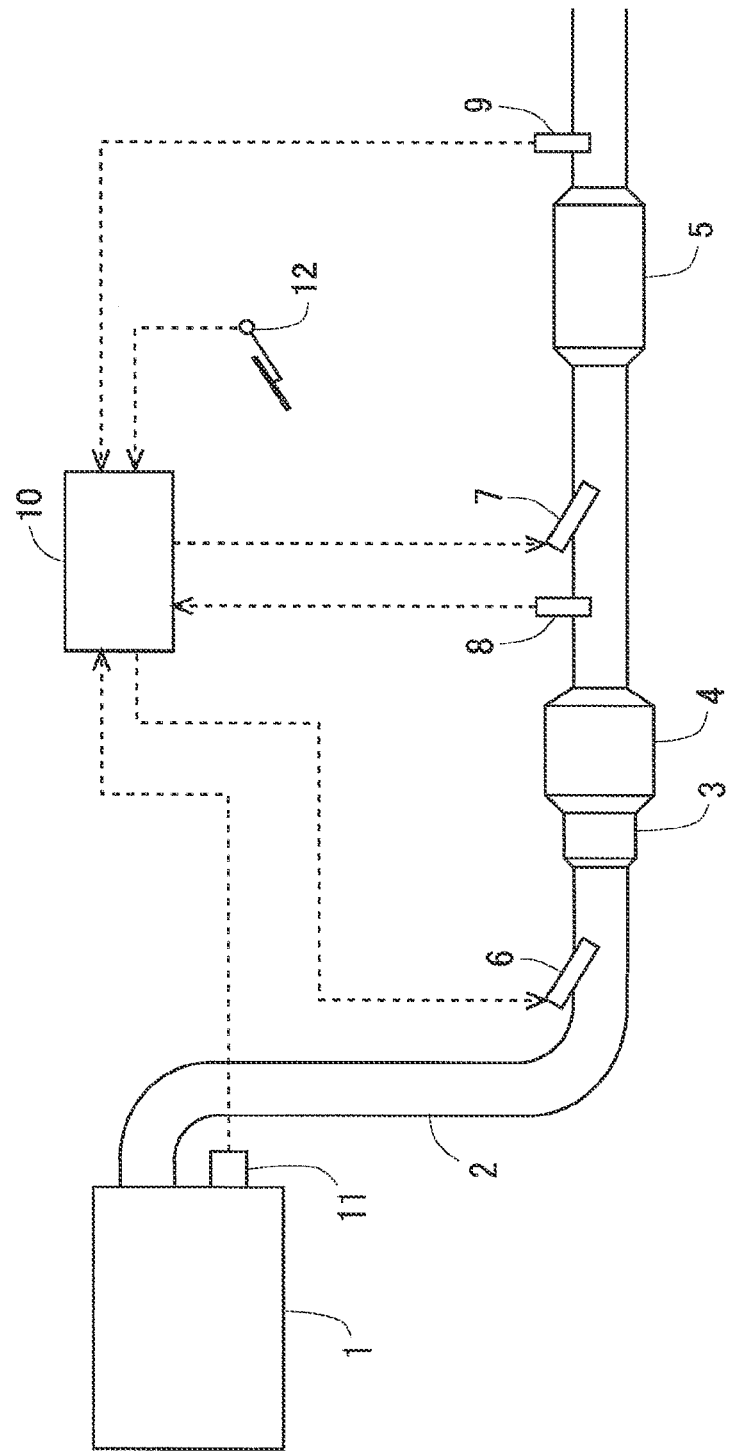
FIG. 1 is a diagrams showing the general configuration of the exhaust system of an internal combustion engine according to an embodiment.

FIG. 1 is a diagram showing the general configuration of an internal combustion engine according to this embodiment and its exhaust system. The internal combustion engine 1 is a diesel engine for driving a vehicle. The internal combustion engine to which the present invention is applied is not limited to a diesel engine but it may be a gasoline or other type of engine. An exhaust passage 2 is connected to the internal combustion engine 1.

A particulate filter (which will be hereinafter referred to as the filter) 4 is provided in the exhaust passage 2. The filter 4 traps particulate matter (PM) in the exhaust gas. An oxidation catalyst 3 is provided as a precatalyst in the exhaust passage 2 upstream of the filter 4. The precatalyst is not limited to an oxidation catalyst, but it may be any catalyst having an oxidizing function (e.g. an NOx storage reduction catalyst). A fuel addition valve 6 is provided in the exhaust passage 2 upstream of the oxidation catalyst 3. The fuel addition valve 6 adds fuel to the exhaust gas.

An NOx selective reduction catalyst (which will be hereinafter referred to as the NOx catalyst) 5 is provided in the exhaust passage 2 downstream of the filter 4. A urea addition valve 7 and a temperature sensor 8 are provided downstream of the filter 4 and upstream of the NOx catalyst 5. The urea addition valve 7 adds aqueous solution of urea to the exhaust gas. With the addition of aqueous solution of urea through the urea addition valve 7, ammonia, which functions as a reducing agent, is supplied to the NOx catalyst 5. The temperature sensor 8 measures the temperature of the exhaust gas flowing into the NOx catalyst 5. A catalyst for oxidizing ammonia may be provided in the exhaust passage 2 downstream of the NOx catalyst 5.

An NOx sensor 9 is provided in the exhaust passage 2 downstream of the NOx catalyst 5. The NOx sensor 9 measures the NOx concentration in the exhaust gas flowing out of the NOx catalyst 5.

An electronic control unit (ECU) 10 for controlling the internal combustion engine 1 is annexed to the internal combustion engine 1. Besides the temperature sensor 8 and the NOx sensor 9, a crank position sensor 11 and an accelerator opening degree sensor 12 are electrically connected to the ECU 10. The crank position sensor 11 measures the crank angle of the internal combustion engine 1. The accelerator opening decree sensor 12 measures the accelerator opening degree of the vehicle on which the internal combustion engine 1 is mounted. Signals output from these sensors are input to the ECU 10.

The ECU 10 calculates the engine speed of the internal combustion engine 1 based on a signal output from the crank position sensor 11. The ECU 10 also calculates the engine load of the internal combustion engine 1 based on a signal output from the accelerator opening degree sensor 12.

Moreover, the fuel addition valve 6 and the urea addition valve 7 are electrically connected to the ECU 10. The operations of these appliances are controlled by the ECU 10.

[Relationship Between Temperature of NOx Catalyst and NOx Removal Rate]

The relationship between the temperature of the NOx catalyst 5 and the NOx purification rate in the NOx catalyst 5 will be described with reference to FIGS. 2 and 3. Here, the NOx purification rate refers to the rate of the quantity of NOx reduced by the NOx catalyst 5 to the quantity of NOx flowing into the NOx catalyst 5. In this embodiment, it is determined that the NOx catalyst 5 is deteriorated when the degree of deterioration of the NOx catalyst 5 is higher than the upper limit of an allowable range. The allowable range of the degree of deterioration of the NOx catalyst 5 can be determined in advance based on, for example, an experiment.

The NOx catalyst 5 has not only the function of reducing NOx but also the function of oxidizing ammonia. FIG. 2 is a graph showing the relationship between the temperature of the NOx catalyst 5 versus the NOx reducing ability and the ammonia oxidizing ability of the NOx catalyst 5. In FIG. 2, the horizontal axis represents the temperature Tc of the NOx catalyst 5, and the vertical axis represents the NOx reducing ability or the ammonia oxidizing ability of the NOx catalyst 5. In FIG. 2, solid curves L1 and L2 represent the NOx reducing ability of the NOx catalyst 5. Solid curve L1 represents the NOx reducing ability of the NOx catalyst 5 in an initial condition. Solid curve L2 represents the NOx reducing ability of the NOx catalyst 5 in a deteriorated condition. Here, the initial condition refers to a condition in which the degree of deterioration of the NOx catalyst 5 is substantially equal to that at the time when the NOx catalyst was installed in the vehicle, namely a condition in which heat deterioration of the NOx catalyst 5 has progressed little. The arrow in FIG. 2 indicates the direction of shift of the NOx reducing ability with the progress of the deterioration of the NOx catalyst 5. Broken curve L3 in FIG. 2 represents the ammonia oxidizing ability of the NOx catalyst 5.

Figure 2:
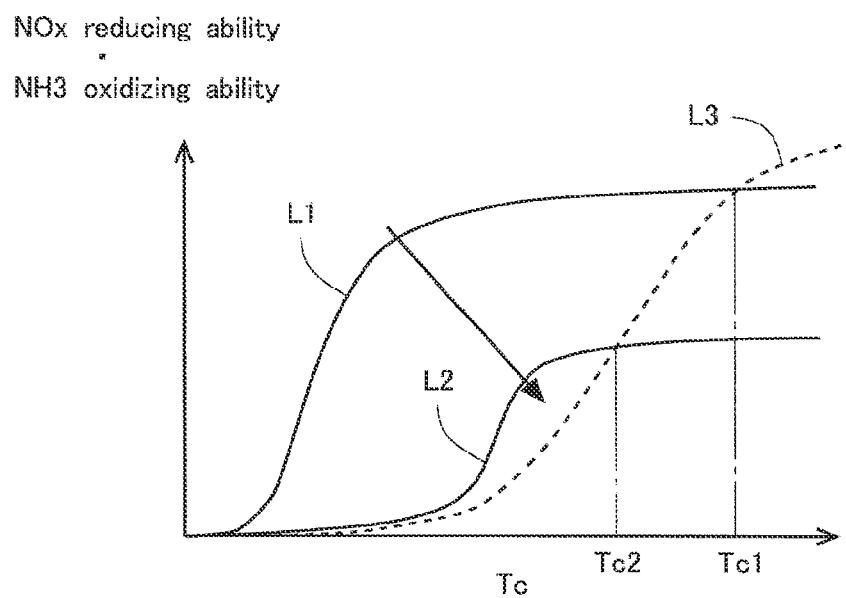
FIG. 2 is a graph showing the relationship between the temperature of the NOx catalyst versus the NOx reducing ability and the ammonia oxidizing ability of the NOx catalyst.
Figure 3:
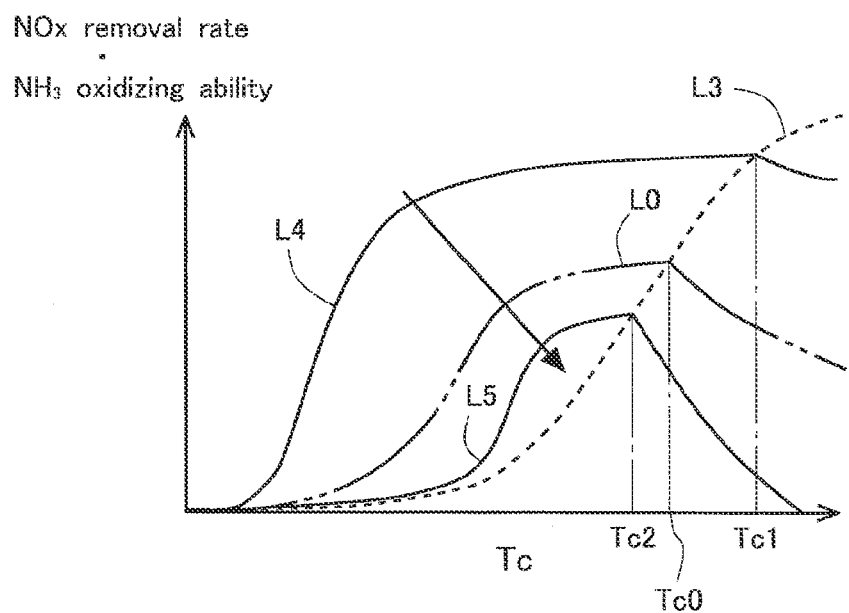
FIG. 3 is a graph showing the relationship between the temperature of the NOx catalyst versus the NOx purification rate in the NOx catalyst.

FIG. 3 is a graph showing the relationship between the temperature of the NOx catalyst 5 versus the NOx purification rate in the NOx catalyst 5. In FIG. 3, the horizontal axis represents the temperature Tc of the NOx catalyst 5, and the vertical axis represents the NOx purification rate in the NOx catalyst 5 or the ammonia oxidation ability of the NOx catalyst 5. In FIG. 3, solid curves L4, L5 and the chain double-dashed curve L0 represents the NOx purification rate in the NOx catalyst 5. Solid curve L4 represents the NOx purification rate in the NOx catalyst 5 in the initial condition. Solid curve L5 represents the NOx purification rate in the NOx catalyst 5 in a deteriorated condition. Chain double-dashed curve L0 represents the NOx purification rate in a condition in which the degree of deterioration of the NOx catalyst 5 is at the upper limit of the allowable range. The arrow in FIG. 3 indicates the direction of shift of the NOx purification rate with the progress in the deterioration of the NOx catalyst 5. Broken curve L3 in FIG. 3 represents the ammonia oxidizing ability of the NOx catalyst 5 as with that in FIG. 2.

As will be seen from FIG. 2, the NOx reducing ability and the ammonia oxidizing ability of the NOx catalyst 5 are both enhanced as the temperature of the NOx catalyst 5 rises. While the temperature of the NOx catalyst 5 is relatively low, the NOx reducing ability is higher than the ammonia oxidizing ability. When the temperature of the NOx catalyst 5 exceeds a certain temperature, the ammonia oxidizing ability becomes higher than the NOx reducing ability.

The NOx reducing ability of the NOx catalyst 5 is degraded as the deterioration of the NOx catalyst 5 progresses. In other words, provided that the temperature of the NOx catalyst 5 is the same, the NOx reducing ability of the NOx catalyst 5 is lower when the degree of deterioration of the NOx catalyst 5 is high than when the degree of deterioration of the NOx catalyst 5 is low. In consequence, the NOx reducing ability of the NOx catalyst 5 in relation to the temperature shifts in the direction indicated by the arrow in FIG. 2 (i.e. in the direction from solid curve L1 to solid curve L2) in accordance with the increase in the degree of deterioration of the NOx catalyst 5.

On the other hand, the ammonia oxidizing ability of the NOx catalyst 5 is hard to be degraded even if the deterioration of the NOx catalyst 5 progresses. Therefore, provided that the temperature of the NOx catalyst 5 is the same, the ammonia oxidizing ability of the NOx catalyst 5 will be the same irrespective of the degree of deterioration of the NOx catalyst 5. In consequence, even when the deterioration of the NOx catalyst 5 progresses, the relationship between the temperature of the NOx catalyst 5 and the ammonia oxidizing ability of the NOx catalyst 5 represented by broken curve L3 in FIG. 2 is maintained. Consequently, as the degree of deterioration of the NOx catalyst 5 increases, the temperature of the NOx catalyst 5 at which the ammonia oxidizing ability exceeds the NOx reducing ability becomes lower, as will be seen from FIG. 2 (Tc2<Tc1).

The oxidation of ammonia generates NOx. Therefore, if the ammonia oxidizing ability of the NOx catalyst 5 becomes higher than its NOx reducing ability, the quantity of NOx flowing out of the NOx catalyst 5 will increase, namely the NOx purification rate in the NOx catalyst 5 will decrease. Consequently, when the temperature of the NOx catalyst 5 reaches the temperature at which the ammonia oxidizing ability exceeds the NOx reducing ability, the NOx purification rate starts to decrease with a rise in the temperature of the NOx catalyst.

As shown in FIG. 2, when the NOx catalyst 5 is in the initial condition, the temperature of the NOx catalyst at which the ammonia oxidizing ability exceeds the NOx reducing ability is Tc1. If the NOx catalyst 5 is deteriorated, the temperature of the NOx catalyst at which the ammonia oxidizing ability exceeds the NOx reducing ability is Tc2. Therefore, if the NOx catalyst 5 is in the initial condition, the NOx purification rate starts to decrease as the temperature of the NOx catalyst 5 reaches Tc1, as will be seen from FIG. 3. On the other hand, if the NOx catalyst 5 is deteriorated, the NOx purification rate starts to decrease as the temperature of the NOx catalyst 5 reaches Tc2.

As described above, temperature Tc2 is lower than temperature Tc1. Therefore, the higher the degree of deterioration of the NOx catalyst 5 is, the lower the temperature (which will be hereinafter referred to as the NOx purification rate decrease temperature) at which the NOx purification rate starts to decrease with a rise in the temperature of the NOx catalyst 5 is.

[Method of Detecting Deterioration of NOx Catalyst]

Next, a method of detecting deterioration of the NOx catalyst according to this embodiment will be described. As described above, in this embodiment it is determined that the NOx catalyst 5 is deteriorated if the degree of deterioration of the NOx catalyst 5 is higher than the upper limit of the allowable range. Here, let Tc0 be the NOx purification rate decrease temperature in the case where the degree of deterioration of the NOx catalyst 5 is at the upper limit of the allowable range, as shown in FIG. 3. In this embodiment, a determination is made as to whether the NOx catalyst 5 is deteriorated or not based on the NOx purification rate in the NOx catalyst 5 at a time when the temperature of the NOx catalyst 5 is higher than Tc0.

When the temperature of the NOx catalyst 5 is higher than Tc0, if the NOx catalyst 5 is deteriorated, the ammonia oxidizing ability thereof has exceeded the NOx reducing ability thereof, and the NOx purification rate has already decreased. In consequence, the difference between the NOx purification rate at that time (i.e. the NOx purification rate in the NOx catalyst 5 in a deteriorated condition) and the NOx purification rate in the NOx catalyst 5 in a normal condition is larger than that at times when the temperature of the NOx catalyst 5 is not higher than the NOx purification rate decrease temperature corresponding to the degree of deterioration at the time.

Thus, determination errors can be prevented by making a determination as to deterioration of the NOx catalyst 5 based on the NOx purification rate at a time when the temperature of the NOx catalyst 5 falls within a temperature range in which the difference between the NOx purification rate in the NOx catalyst 5 in a normal condition and the NOx purification rate in the NOx catalyst 5 in a deteriorated condition is relatively large. In consequence, the method of detecting deterioration of the NOx catalyst according to this embodiment can provide more accurate detection of deterioration of the NOx catalyst 5.

[Deterioration Detection Process]

In the following, a process of detecting deterioration of NOx catalyst according to this embodiment will be described with reference to the flow chart of FIG. 4. This process is stored in the ECU 10 in advance and executed repeatedly by the ECU 10 at regular intervals while aqueous solution of urea is added through the urea addition valve 7.

In this process, first in step S101, the temperature Tc of the NOx catalyst 5 is calculated. The temperature of he NOx catalyst 5 can be calculated based on the measurement value of the temperature sensor 8. Alternatively, the temperature of the NOx catalyst 5 may be estimated based on the operation state (the engine load and engine speed etc.) of the internal combustion engine 1. In cases where a temperature sensor is provided in the exhaust passage downstream of the NOx catalyst 5, the temperature of the NOx catalyst 5 can be calculated based on the measurement value of this temperature sensor. Still alternatively, a temperature sensor may be provided in the NOx catalyst 5, and the temperature of the NOx catalyst 5 may be measured by this temperature sensor.

Then in step S102, it is determined whether or not the temperature Tc of the NOx catalyst 5 is higher than the NOx purification rate decrease temperature Tc0 with the NOx catalyst 5 of which the degree of deterioration is at the upper limit of the allowable range (or the NOx purification rate decrease temperature Tc0 that the NOx catalyst 5 will have when the degree of deterioration thereof is at the upper limit of the allowable range). The NOx purification rate decrease temperature Tc0 with the NOx catalyst 5 of which the degree of deterioration is at the upper limit of the allowable range has been obtained in advance by, for example, an experiment and stored in the ECU 10.

If the determination in step S102 is negative, the execution of this process is once terminated. On the other hand, if the determination in step S102 is affirmative, the NOx purification rate Pnox in the NOx catalyst 5 is calculated next in step S103.

The NOx purification rate Pnox in the NOx catalyst 5 is calculated based on the NOx concentration in the exhaust gas flowing into the NOx catalyst 5 and the NOx concentration in the exhaust gas flowing out of the NOx catalyst 5. The NOx concentration in the exhaust gas flowing into the NOx catalyst 5 can be estimated based on the operation state of the internal combustion engine 1. Alternatively, an NOx sensor may be provided in the exhaust passage 2 upstream of the NOx catalyst 5, and the NOx concentration in the exhaust gas flowing into the NOx catalyst 5 may be measured by this NOx sensor. The NOx concentration of the exhaust gas flowing out of the NOx catalyst 5 can be measured by the NOx sensor 9.

Then in step S104, the NOx purification rate at the time when the degree of deterioration of the NOx catalyst 5 is at the upper limit of the allowable range and the NOx catalyst 5 has the temperature Tc calculated in step S101 is calculated, namely the threshold value of the NOx purification rate Pnox0 (which will be hereinafter referred to as the normality determination threshold value) that allows the determination that the NOx catalyst 5 is in a normal condition is calculated. The relationship between the NOx purification rate and the temperature of the NOx catalyst 5 at the time when the degree of deterioration of the NOx catalyst 5 is at the upper limit of the allowable range is stored in the ECU 10 in advance as a map like that shown in FIG. 3 (the chain double-dashed curve in FIG. 3) or as a function. In step S104, the normality determination threshold value Pnox0 is calculated using this map or function.

Then in step S105, it is determined whether or not the NOx purification rate Pnox calculated in step S103 is lower than the normality determination threshold value Pnox0 calculated in step S104. If the determination in step S105 is affirmative, it is determined next in step S106 that the NOx catalyst 5 is deteriorated. On the other hand, if the determination in step S105 is negative, it is determined next in step S107 that the NOx catalyst 5 is in a normal condition.

[Modification 1]

In the following, a method of detecting deterioration of an NOx catalyst according to a first modification of this embodiment will be described. In this modification, a determination as to whether the NOx catalyst 5 is deteriorated or not is made based on the NOx purification rate in the NOx catalyst 5 at the time when the temperature of the NOx catalyst 5 is at the NOx purification rate decrease temperature with the NOx catalyst 5 that is in the initial condition (i.e. Tc1 in FIGS. 2 and 3).

As shown in FIG. 3, even if the NOx catalyst 5 is in a normal condition, the NOx purification rate decreases with a rise in the temperature of the NOx catalyst 5 when the temperature of the NOx catalyst 5 exceeds the NOx purification rate decrease temperature Tc1 with the NOx catalyst 5 that is in the initial condition. Consequently, the difference between the NOx purification rate in the NOx catalyst 5 in a normal condition and the NOx purification rate in the NOx catalyst 5 in a deteriorated condition decreases gradually with a rise in the temperature of the NOx catalyst 5. Therefore, if the determination as to deterioration of the NOx catalyst 5 is performed at a time when the temperature of the NOx catalyst 5 is equal to the NOx purification rate decrease temperature Tc1 with the NOx catalyst 5 that is in the initial condition, the determination as to deterioration of the NOx catalyst 5 can be performed at the time when the difference between the NOx purification rate in the NOx catalyst 5 in a normal condition and the NOx purification rate in the NOx catalyst 5 in a deteriorated condition is as large as possible. In consequence, deterioration of the NOx catalyst 5 can be detected with improved accuracy.

In the following, a process of detecting deterioration of NOx catalyst according to this modification will be described with reference to the flow chart of FIG. 5. This process is stored in the ECU 10 in advance and executed repeatedly by the ECU 10 at regular intervals while aqueous solution of urea is added through the urea addition valve 7. In this process, steps S102 in the process shown in FIG. 4 is replaced by step S202. So only the processing in step S202 will be described, and the processing in the other steps will not be described.

In this process, the processing of step S202 is executed after step S101. In step S202, it is determined whether or not the temperature Tc of the NOx catalyst 5 is equal to the NOx purification rate decrease temperature Tc1 with the NOx catalyst 5 that is in the initial condition. The NOx purification rate decrease temperature Tc1 with the NOx catalyst 5 that is in the initial condition has been determined in advance by, for example, an experiment and stored in the ECU 10.

If the determination in step S202 is negative, the execution of this process is once terminated. On the other hand, if the determination in step S202 is affirmative, the processing of step S103 is executed next.

[Modification 2]

In the following, a method of detecting deterioration of an NOx catalyst according to a second modification of this embodiment will be described. In this modification, a determination as to whether the NOx catalyst 5 is deteriorated or not is made based on the NOx purification rate in the NOx catalyst 5 at the time when the temperature of the NOx catalyst 5 is higher than the NOx purification rate decrease temperature Tc0 with the NOx catalyst 5 of which the degree of deterioration is at the upper limit of the allowable range and not higher than the temperature at which the NOx purification rate in the NOx catalyst 5 of which the degree of deterioration is at the upper limit of the allowable range will become zero.

If the temperature of the NOx catalyst 5 of which the degree of deterioration is at the upper limit of the allowable range rises beyond the NOx purification rate decrease temperature Tc0, the NOx purification rate decreases with the rise in the temperature. Eventually, the NOx purification rate becomes zero when the temperature of the NOx catalyst 5 reaches a certain temperature Tc3. In the temperature range equal to or higher than the temperature Tc3 at which the NOx purification rate in the NOx catalyst 5 of which the degree of deterioration is at the upper limit of the allowable range will become zero, the NOx purification rate is zero if the NOx catalyst 5 is deteriorated.

On the other hand, even when the degree of deterioration of the NOx catalyst 5 is lower than the upper limit of the allowable range, the NOx purification rate starts to decrease with a rise in the temperature of the NOx catalyst 5 as the temperature of the NOx catalyst 5 rises beyond the NOx purification rate decrease temperature Tc0 with the NOx catalyst 5 of which the degree of deterioration is at the upper limit of the allowable range to reach the NOx purification rate decrease temperature corresponding to the actual degree of deterioration of the NOx catalyst 5.

In the temperature range in which the NOx purification rate is zero when the degree of deterioration of the NOx catalyst is higher than the upper limit of the allowable range (namely, when the NOx catalyst is deteriorated), and the NOx purification rate decreases with a rise in the temperature of the NOx catalyst 5 when the degree of deterioration of the NOx catalyst 5 is lower than the upper limit of the allowable range (namely, when the NOx catalyst is in a normal condition), namely in the range of the temperature of the NOx catalyst 5 higher than Tc3, the difference between the NOx purification rate in the NOx catalyst 5 in a normal condition and the NOx purification rate in the NOx catalyst 5 in a deteriorated condition gradually decreases as the temperature of the NOx catalyst 5 rises.

Therefore, if the determination as to deterioration of the NOx catalyst 5 is performed at a time when the temperature of the NOx catalyst 5 is higher than the NOx purification rate decrease temperature Tc0 with the NOx catalyst 5 of which the degree of deterioration is at the upper limit of the allowable range and not higher than the temperature Tc3 at which the NOx purification rate in the NOx catalyst 5 of which the degree of deterioration is at the upper limit of the allowable range will become zero, the determination as to deterioration of the NOx catalyst 5 can be performed at the time when the difference between the NOx purification rate in the NOx catalyst 5 in a normal condition and the NOx purification rate in the NOx catalyst 5 in a deteriorated condition is as large as possible. In consequence, deterioration of the NOx catalyst 5 can be detected with improved accuracy.

Figure 6:
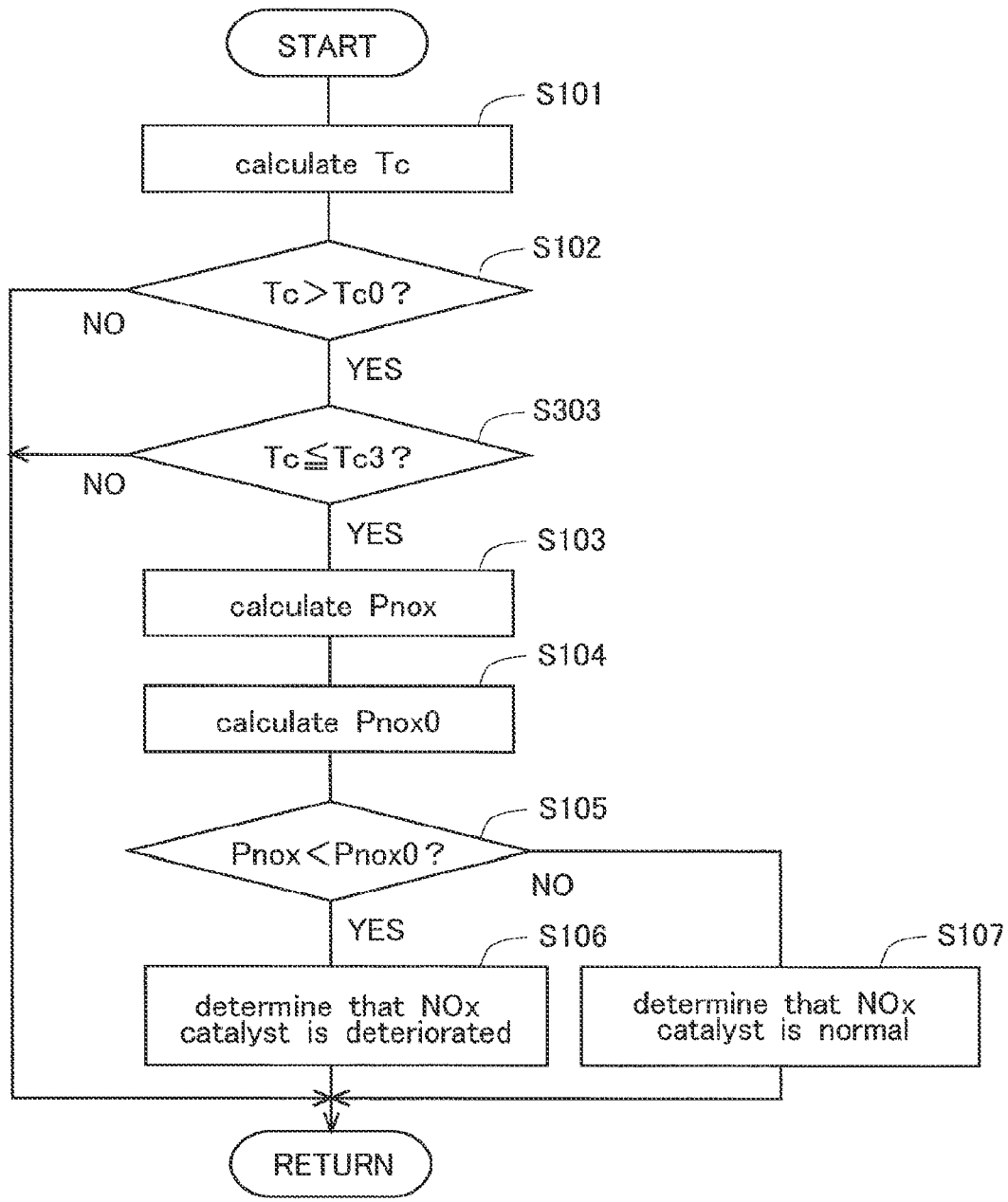
FIG. 6 is a flow chart of a process of detecting deterioration of NOx catalyst according to a second modification of embodiment 1.

In the following, a process of detecting deterioration of NOx catalyst according to this modification will be described with reference to the flow chart of FIG. 6. This process is stored in the ECU 10 in advance and executed repeatedly by the ECU 10 at regular intervals while aqueous solution of urea is added through the urea addition valve 7. In this process, the process shown in FIG. 4 is augmented to include step S303. So only the processing in step S303 will be described, and the processing in the other steps will not be described.

In this process, if the determination in step S102 is affirmative, the processing in step S303 is executed next. In step S303, it is determined whether or not the temperature of the NOx catalyst 5 is equal to or lower than the temperature Tc3 at which the NOx purification rate in the NOx catalyst 5 of which the degree of deterioration is at the upper limit of the allowable range will become zero. The temperature Tc3 at which the NOx purification rate in the NOx catalyst 5 of which the degree of deterioration is at the upper limit of the allowable range will become zero has been obtained in advance based on, for example, an experiment and stored in the ECU 10.

If the determination in step S303 is negative, the execution of this process is once terminated. On the other hand, if the determination in step S303 is affirmative, namely if the temperature of the NOx catalyst 5 is higher than Tc0 and not higher than Tc3, the processing of step S103 is executed next.

<Embodiment 2>
[Method of Detecting Deterioration of NOx Catalyst]

The basic configuration of the exhaust system of the internal combustion engine according to this embodiment is the same as that in embodiment 1. In the following, the method of detecting deterioration of the NOx catalyst according to this embodiment will be described. As described before, the higher the degree of deterioration of the NOx catalyst 5 is, the lower the NOx purification rate decrease temperature is. In view of this, in this embodiment, a determination as to whether the NOx catalyst 5 is deteriorated or not is made based on the NOx purification rate decrease temperature. Specifically, if the NOx purification rate decrease temperature is lower than the NOx purification rate decrease temperature Tc0 with the NOx catalyst 5 of which the degree of deterioration is at the upper limit of the allowable range, it is determined that the NOx catalyst 5 is deteriorated.

In this embodiment also, as with the first embodiment, the NOx purification rate in the NOx catalyst 5 is calculated based on the NOx concentration in the exhaust gas flowing into the NOx catalyst 5 and the NOx concentration in the exhaust gas flowing out of the NOx catalyst 5. The NOx concentration in the exhaust gas flowing into the NOx catalyst 5 is estimated based on the operation state of the internal combustion engine 1. Alternatively, an NOx sensor may be provided in the exhaust passage 2 upstream of the NOx catalyst 5, and the NOx concentration in the exhaust gas flowing into the NOx catalyst 5 may be measured by this NOx sensor. The NOx concentration of the exhaust gas flowing out of the NOx catalyst 5 is measured by the NOx sensor 9.

It follows from the above that if the estimated or measured value of the NOx concentration in the exhaust gas has an error, the value of the NOx purification rate calculated based on the NOx concentration will also have an error. However, even if the value of the NOx purification rate has an error, the value of the NOx purification rate decrease temperature obtained based on the change in the NOx purification rate with the change in the temperature of the NOx catalyst 5 will not vary. Therefore, the determination of deterioration of the NOx catalyst 5 based on the NOx purification rate decrease temperature can provide more accurate detection of deterioration of the NOx catalyst 5.

[Deterioration Detection Process]

Figure 7:
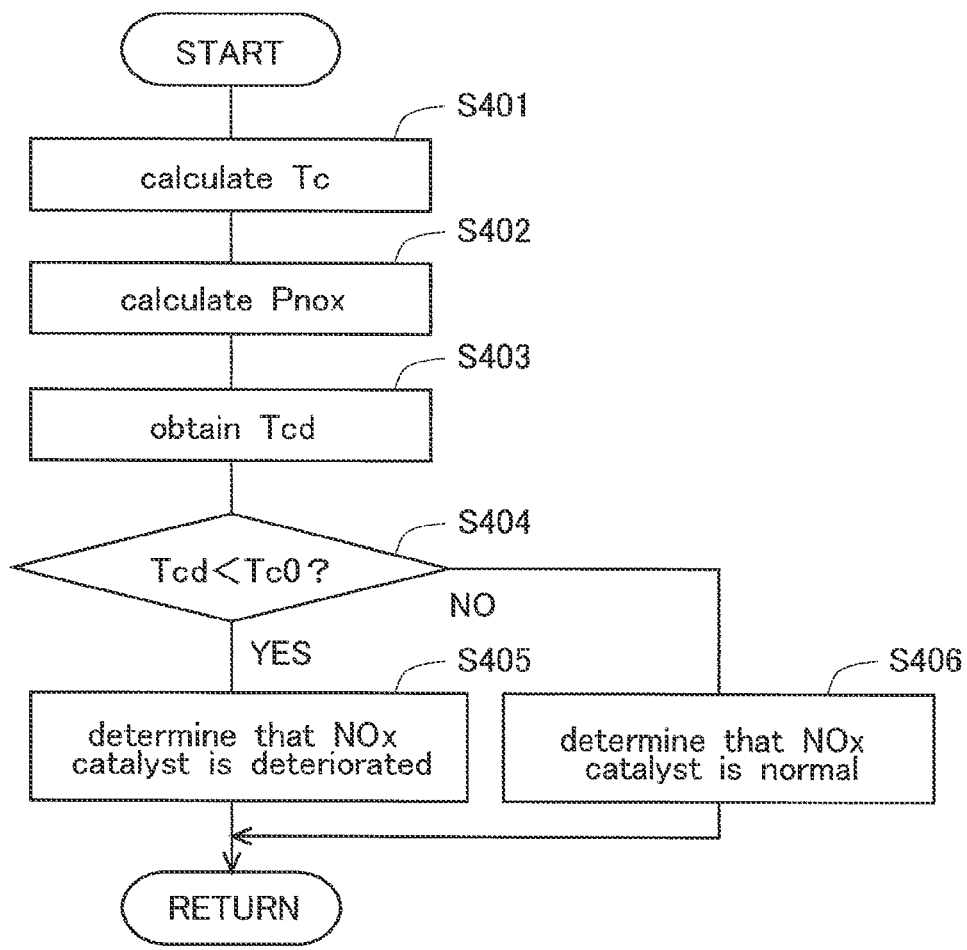
FIG. 7 is a flow chart of a process of detecting deterioration of NOx catalyst according to embodiment 2.

In the following, a process of detecting deterioration of NOx catalyst according to this embodiment will be described with reference to the flow chart of FIG. 7. This process is stored in the ECU 10 in advance and executed repeatedly by the ECU 10 at regular intervals while aqueous solution of urea is added through the urea addition valve 7.

Figure 4:
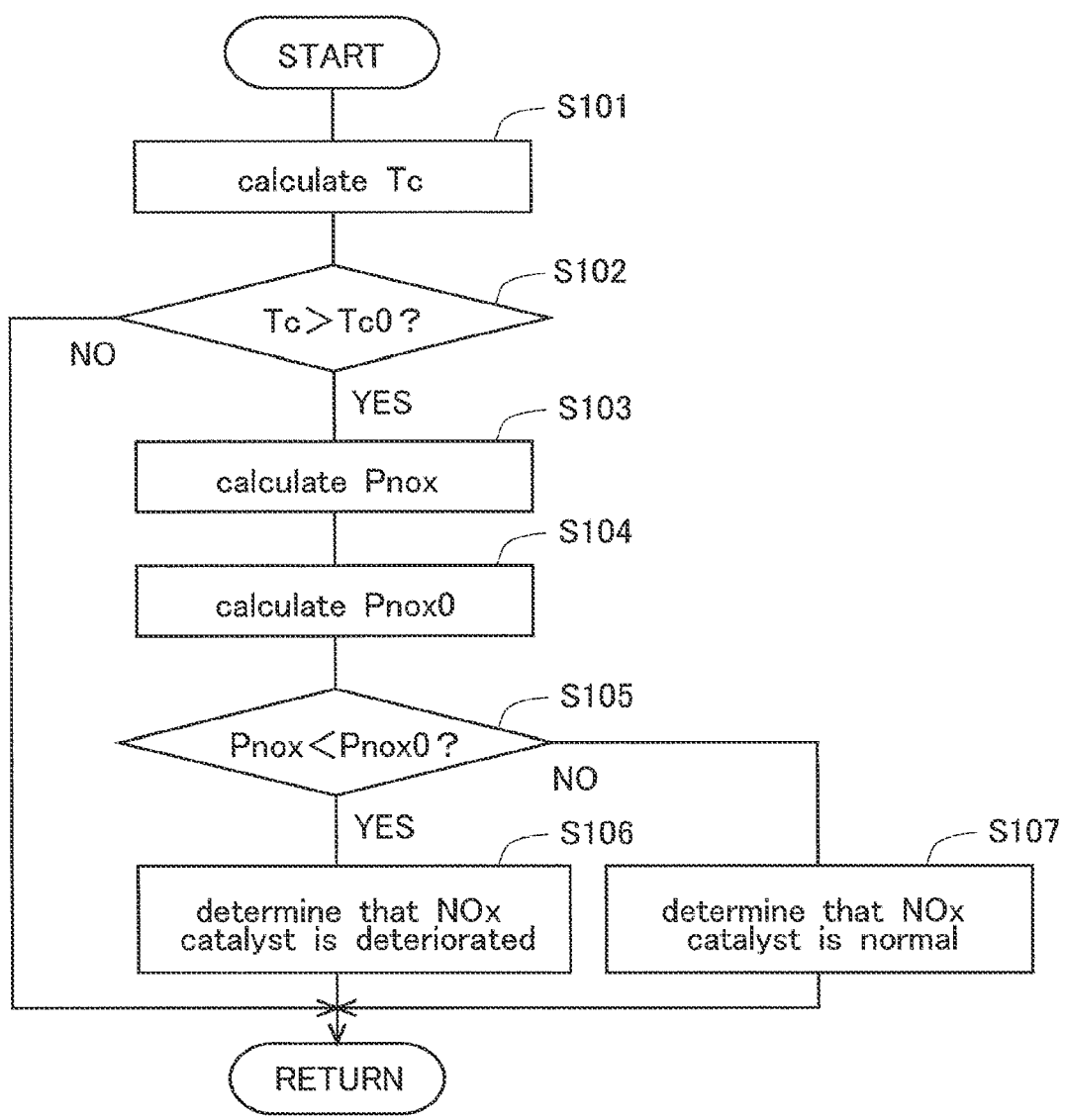
FIG. 4 is a flow chart of a process of detecting deterioration of NOx catalyst according to embodiment 1.
Figure 5:
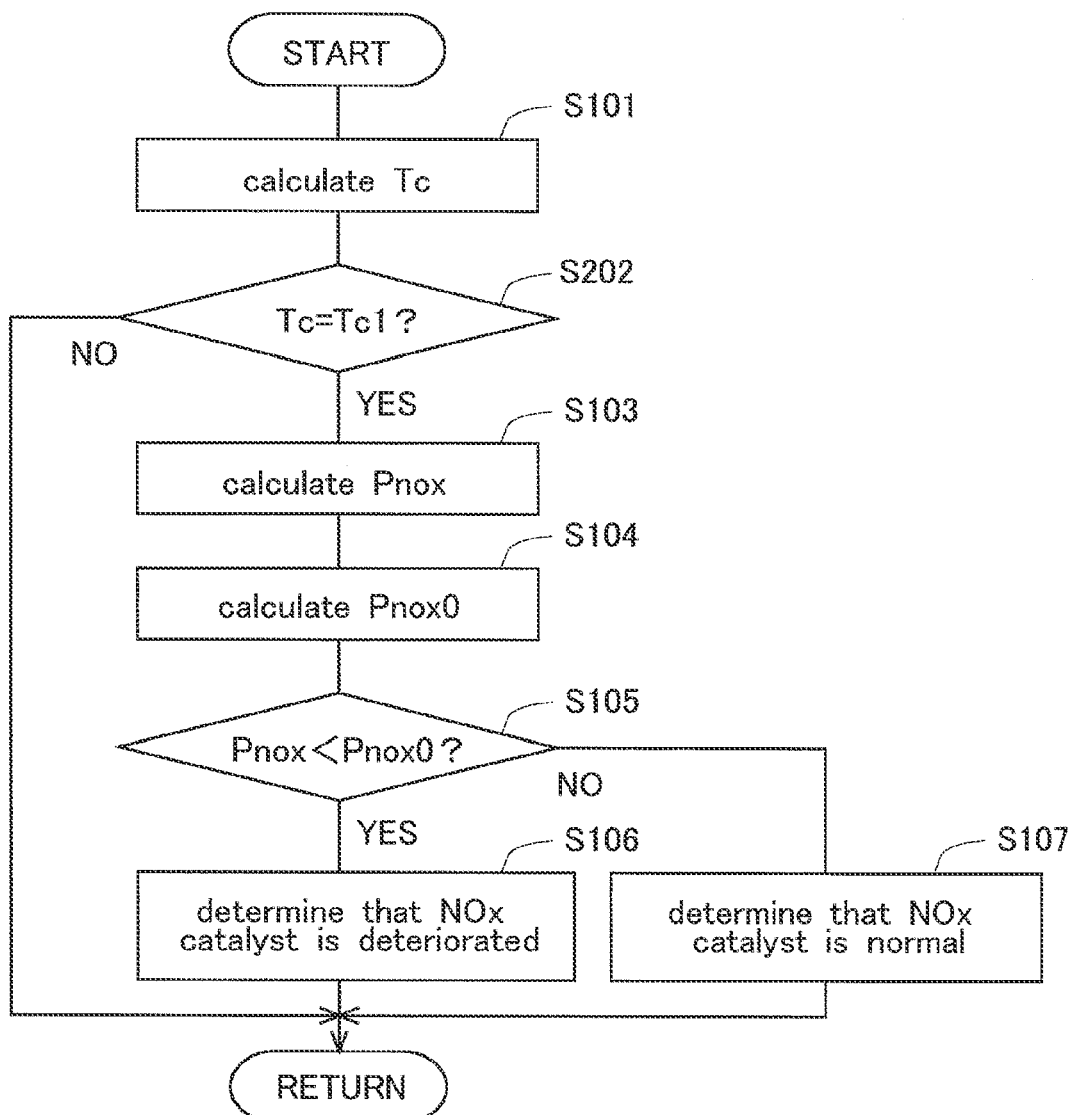
FIG. 5 is a flow chart of a process of detecting deterioration of NOx catalyst according to a first modification of embodiment 1.

In this process, first in step S401, the temperature Tc of the NOx catalyst 5 is calculated in the manner same as step S101 in the process shown in FIG. 4. Then in step S402, the NOx purification rate Pnox in the NOx catalyst 5 is calculated in the same manner as step S103 in the process shown in FIG. 4.

The NOx purification rate Pnox calculated in step S402 is associated with the temperature Tc of the NOx catalyst 5 calculated in step S401 and stored in the ECU 10. The temperature Tc of the NOx catalyst 5 changes with the change in the temperature of the exhaust gas flowing into the NOx catalyst 5. Therefore, the relationship between the temperature Tc of the NOx catalyst 5 and the NOx purification rate Pnox like that shown in FIG. 3 can be obtained by calculating the temperature Tc of the NOx catalyst 5 and the NOx purification rate Pnox associated with the temperature and storing them for a certain period of time. In order to make a determine as to deterioration of the NOx catalyst 5, the relationship between the temperature Tc of the NOx catalyst 5 and the NOx purification rate Pnox may be obtained by forcedly varying the temperature Tc of the NOx catalyst 5 and calculating NOx purification rates Pnox associated with different temperatures.

Then in step S403, the NOx purification rate decrease temperature Tcd is obtained based on the relationship between the temperature Tc of the NOx catalyst 5 and the NOx purification rate Pnox. The NOx purification rate decrease temperature Tcd obtained in this step is the NOx purification rate decrease temperature corresponding to the degree of deterioration of the NOx catalyst 5 at the time.

Then in step S404, it is determined whether or not the NOx purification rate decrease temperature Tcd obtained in step S403 is lower than the NOx purification rate decrease temperature Tc0 with the NOx catalyst 5 of which the degree of deterioration is at the upper limit of the allowable range. The NOx purification rate decrease temperature Tc0 with the NOx catalyst 5 of which the degree of deterioration is at the upper limit of the allowable range has been obtained in advance by, for example, an experiment and stored in the ECU 10.

If the determination in step S404 is affirmative, it is determined next in step S405 that the NOx catalyst 5 is deteriorated. On the other hand, if the determination in step S404 is negative, it is determined next in step S406 that the NOx catalyst 5 is in a normal condition.

DESCRIPTION OF THE REFERENCE SYMBOLS

1: internal combustion engine
2: exhaust passage
3: oxidation catalyst
4: particulate filter (filter)
5: NOx selective reduction catalyst (NOx catalyst)
6: fuel addition valve
7: urea addition valve
8: temperature sensor
9: NOx sensor
10: ECU
11: crank position sensor
12: accelerator opening degree sensor
15: downstream exhaust gas temperature sensor

The invention claimed is:

1. An apparatus for detecting deterioration of NOx selective reduction catalyst provided in an exhaust passage of an internal combustion engine, the apparatus comprising:

an ammonia supplying unit that supplies ammonia serving as a reducing agent to said NOx selective reduction catalyst;
a temperature obtaining unit that obtains the temperature of the NOx selective reduction catalyst;
a computer comprising at least one processor configured to:
determine whether the temperature of said NOx selective reduction catalyst is more than a predetermined temperature, wherein the predetermined temperature is a temperature at which a NOx purification rate will start to decrease with a rise in the temperature of said NOx selective reduction catalyst if a degree of deterioration of said NOx selective reduction catalyst is at an upper limit of a predetermined allowable range, wherein the NOx purification rate decrease temperature occurs at a predetermined time when the temperature of the NOx selective reduction catalyst reaches a temperature at which an ammonia oxidizing ability exceeds a NOx reducing ability of the NOx selective reduction catalyst;
based on the temperature of said NOx selective reduction catalyst being more than the predetermined temperature, calculate the NOx purification rate in said NOx selective reduction catalyst based on the NOx concentration in exhaust gas flowing into said NOx selective reduction catalyst and the NOx concentration in exhaust gas flowing out of said NOx selective reduction catalyst; and
determine whether the NOx purification rate calculated at the predetermined time is less than a threshold value, the predetermined time corresponding to when the temperature of the NOx selective reduction catatyst is more than the predetermined temperature, and determine whether or not said NOx selective reduction catalyst is deteriorated based on the determination result.

2. An apparatus for detecting deterioration of NOx selective reduction catalyst according to claim 1, wherein said computer comprising at least one processor determines whether or not said NOx selective reduction catalyst is deteriorated based on the NOx purification rate calculated by said NOx purification rate calculation unit at a time when the temperature of said NOx selective reduction catalyst is equal to a temperature at which the NOx purification rate will start to decrease with a rise in the temperature of said NOx selective reduction catalyst if said NOx selective reduction catalyst is in an initial condition.

3. An apparatus for detecting deterioration of NOx selective reduction catalyst according to claim 1, wherein said computer comprising at least one processor determines whether or not said NOx selective reduction catalyst is deteriorated based on the NOx purification rate calculated by said NOx purification rate calculation unit at a time when the temperature of said NOx selective reduction catalyst is higher than said predetermined temperature and not higher than a temperature at which the NOx purification rate in said NOx selective reduction catalyst will become zero if the degree of deterioration of said NOx selective reduction catalyst is at the upper limit of the allowable range.

4. An apparatus for detecting deterioration of NOx selective reduction catalyst provided in an exhaust passage of an internal combustion engine, comprising:
an ammonia supplying unit that supplies ammonia serving as a reducing agent to said NOx selective reduction catalyst;

a temperature obtaining unit that obtains the temperature of the NOx selective reduction catalyst;

a computer comprising at least one processor configured to:

calculate the NOx purification rate in said NOx selective reduction catalyst based on the NOx concentration in exhaust gas flowing into said NOx selective reduction catalyst and the NOx concentration in exhaust gas flowing out of said NOx selective reduction catalyst;

determine a NOx purification rate decrease temperature based on a temperature of the NOx selective reduction catalyst and the NOx purification rate, wherein the NOx purification rate decrease temperature is a temperature at which the NOx purification rate starts to decrease with a rise in the temperature of the NOx selective reduction catalyst, and is when the NOx selective reduction catalyst reaches a temperature at which an ammonia oxidizing ability exceeds a NOx reducing ability of the NOx selective reduction catalyst;

determine that said NOx selective reduction catalyst is deteriorated if the NOx purification rate decrease temperature is lower than a predetermined criterion temperature.

5. An apparatus for detecting deterioration of NOx selective reduction catalyst according to claim 4, wherein said predetermined criterion temperature is a temperature at which the NOx purification rate will start to decrease with a rise in the temperature of said NOx selective reduction catalyst if the degree of deterioration of said NOx selective reduction catalyst is at the upper limit of an allowable range.

* * * * *